US009386786B2

(12) United States Patent
Kimura et al.

(10) Patent No.: US 9,386,786 B2
(45) Date of Patent: *Jul. 12, 2016

(54) EQUOL-CONTAINING FERMENTATION PRODUCT OF SOYBEAN EMBRYONIC AXIS, AND METHOD FOR PRODUCTION THEREOF

(75) Inventors: Hiroyuki Kimura, Saga (JP); Takeshi Yamauchi, Shiga (JP); Tomomi Ueno, Saga (JP); Toshimi Suzuki, Saga (JP); Kentaro Tadano, Saga (JP); Ikutaro Sato, Saga (JP); Shigeto Uchiyama, Saga (JP); Masahiro Oono, Saitama (JP); Masatoshi Mizuno, Shiga (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/549,686

(22) Filed: Jul. 16, 2012

(65) Prior Publication Data

US 2012/0277303 A1 Nov. 1, 2012

Related U.S. Application Data

(63) Continuation of application No. 12/095,828, filed as application No. PCT/JP2006/324255 on Dec. 5, 2006.

(30) Foreign Application Priority Data

Dec. 6, 2005 (JP) ................................. 2005-352337
Oct. 11, 2006 (JP) ................................. 2006-277934

(51) Int. Cl.
| A61K 8/97 | (2006.01) |
| A23L 1/20 | (2006.01) |
| A23L 1/30 | (2006.01) |
| A61K 8/49 | (2006.01) |
| A61Q 19/00 | (2006.01) |
| A61Q 19/02 | (2006.01) |
| A61Q 19/10 | (2006.01) |

(52) U.S. Cl.
CPC ............. *A23L 1/2008* (2013.01); *A23L 1/3002* (2013.01); *A61K 8/498* (2013.01); *A61K 8/97* (2013.01); *A61Q 19/00* (2013.01); *A23V 2002/00* (2013.01); *A61K 2800/85* (2013.01); *A61Q 19/02* (2013.01); *A61Q 19/10* (2013.01)

(58) Field of Classification Search
None
See application file for complete search history.

(56) References Cited

U.S. PATENT DOCUMENTS

| 6,579,711 | B1 | 6/2003 | Gaier et al. |
| 6,716,424 | B1 | 4/2004 | Uchiyama et al. |
| 7,939,060 | B2 | 5/2011 | Uchiyama et al. |
| 8,003,092 | B2 | 8/2011 | Yamamoto et al. |
| 2002/0160079 | A1 | 10/2002 | Kim et al. |
| 2004/0141954 | A1 | 7/2004 | Uchiyama et al. |
| 2006/0148045 | A1 | 7/2006 | Uchiyama et al. |
| 2012/0277303 | A1 | 11/2012 | Kimura et al. |

FOREIGN PATENT DOCUMENTS

| CA | 2298679 A1 | 2/1999 |
| CA | 2531173 A1 | 1/2005 |
| EP | 0 988 793 A1 | 3/2000 |
| EP | 1 054 008 A1 | 11/2000 |
| EP | 1 649 760 A1 | 4/2006 |
| JP | 7-61241 B2 | 7/1995 |
| JP | 2002-234844 A | 8/2002 |
| JP | 2004-33092 A | 2/2004 |
| JP | 2004-236523 A | 8/2004 |
| JP | 2014-54234 A | 3/2014 |
| WO | 99/07392 A1 | 2/1999 |
| WO | 2004-002501 | 1/2004 |
| WO | 2004/009035 A2 | 1/2004 |
| WO | 2005/000042 A1 | 1/2005 |
| WO | 2007/066655 A1 | 6/2007 |

OTHER PUBLICATIONS

Saitoh et al., Biochimica et Biophysica Acta 1674 (2004) 122-130.*
Extended European Search Report dated Dec. 23, 2009 in European Application No. 06834010.8-2114.
Nam Ju Kim, et al., "Effect of Bifidobacterium-fermented Soy Hypocotyls Intake on the Composition of Human Large Intestinal Bacteria in the Elderly", Food Science and Biotechnology, Korean Society of Food Science and Technology, vol. 12, No. 2, pp. 178-179 (2003).
Search Report and Written Opinion dated Aug. 12, 2010 on Singapore Application No. 200804067-7.
Office Action dated Jan. 4, 2011 on Canadian Patent Application No. 2,631,850.
Office Action dated Jan. 5, 2012 on Philippines Patent Application No. 01-2008-501281.
Office Action issued May 23, 2012, in EP Application No. 06834010.8 (in the name of Otsuka Pharmaceutical Co., Ltd.).
Mariko Uehara et al., "Transformation of Daidzein to Equol and Its Bioactivity", Functional Food and Health, American Chemical Society, 2008, 993: 81-89.
Jin Park et al., "Formononetin, a phyto-oestrogen, and its metabolites up-regulate interleukin-4 production in activated T cells via increased AP-1, DNA binding activity", Immunology, Sep. 2005, 116(1), p. 71-81.
Chinese Office Action, dated Jun. 5, 2014, issued in counterpart Chinese Patent Application No. 201210239156.6.
Yabin Xia et al., "Food Chemistry". China Light Industry Press, Jun. 30, 2001, p. 321.

(Continued)

*Primary Examiner* — Irene Marx
(74) *Attorney, Agent, or Firm* — Sughrue Mion, PLLC

(57) ABSTRACT

An object of the invention is to provide an equol-containing fermented soybean hypocotyl material that is useful for foods, pharmaceutical preparations, cosmetic products, etc. The equol-containing fermented soybean hypocotyl material of the invention is obtained by fermenting soybean hypocotyls using at least one microorganism having an equol-producing ability by utilizing at least one daidzein compound selected from the group consisting of diadzein glycosides, daidzein, and dihydrodaidzein.

3 Claims, 4 Drawing Sheets

(56) References Cited

OTHER PUBLICATIONS

Widyarini et al., "Protective Effect of the Isoflavanoid Equol Against Hairless Mouse Skin Carcinogenesis Induced by UV Radiation Alone or with a Chemical Cocarcinogen," Photochemistry and Photobiology, 2005, 81: 32-37.
Gokmen et al., "Significance of Arginase and Ornithine in Malignant Tumors of the Human Skin," J. Lab. Clin. Med., 2001, 137: 340-4.
Office Action dated Aug. 13, 2015, issued by the United States Patent and Trademark Office in U.S. Appl. No. 13/549,568.
Ling, G., "Anti-oxidization Foods and Health," Chemical Industry Press, May 4, 2004, pp. 217-219.
Liu, Z., "Food Nutriology," $2^{nd}$ Edition, Beijing China Light Industry Press, Apr. 2004, p. 232.
Shi, Y, "Soybean Product Processing Technology," $2^{nd}$ Edition, China Light Industry Press, Jun. 2005, pp. 36-38.
Cui, H, "Soybean Isoflavones: Research and Application of Their Activities," Science Press, Apr. 2005, pp. 188-189.
Ito Akihiro et al., The Journal of Japan Mibyou System Association, 2002, vol. 8, No. 2, 6 pages total.
Kyoichi Kishi, Shikoku Acta Medica, 2002, vol. 58, No. 4-5, pp. 189-193, "Are amino acids effective for dieting?", 8 pages total.
Miho Komatsu, Food Processing and Ingredients, 2005, vol. 40, No. 11, pp. 62-64, "Research on the Function of Ornithine", 7 pages total.
Mariko Uehara, Journal of Clinical and Experimental Medicine (Igaku No Ayumi), 2004, vol. 208, No. 12, pp. 996-1000, "Antioxidative efficacy of flavonoids", 8 pages total.
Japanese Journal of Nutritional Assessment, 2005, vol. 22, No. 2, pp. 151-154, "Soybean isoflavone", 6 pages total.
Setchell et al., "The Clinical Importance of the Metabolite Equol—A Clue to the Effectiveness of Soy and Its Isoflavones", The Journal of Nutrition, 2002, vol. 132, pp. 3577-3584.
Dastidar et al., "Studies on the antibacterial potentiality of isoflavones", International Journal of Antimicrobial Agents, vol. 23, (2004), pp. 99-102.
Communication, dated Oct. 27, 2015, issued by the Japanese Patent Office in counterpart Japanese Patent Application No. 2014-083507.
Brian J. B. Wood, "Microbiology of Fermented Foods", second edition, Advanced Food Science and Technology in US—VI, China Light Industry Press, Jul. 7, 2001, p. 66 (5 pgs. total).
Editor Committee of Basic Medicine, "Chinese Medical Encyclopedia Basic Medicine", Shanghai Science and Technology Press, Dec. 1998, pp. 222-223 (7 pgs. total).
James, F. B, Phyllis A. B., "Prescription for Nutritional Healing", Beijing World Publishing Corporation, Sep. 2000, p. 466 (5 pgs. total).

* cited by examiner

EQUOL-CONTAINING FERMENTATION PRODUCT OF SOYBEAN EMBRYONIC AXIS, AND METHOD FOR PRODUCTION THEREOF

This is a Continuation Application of U.S. application Ser. No. 12/095,828 filed Jun. 24, 2009, which is a U.S. National Stage Entry of PCT/JP2006/324255 filed Dec. 5, 2006, which claims priority from JP Patent Appln. No. 2005-352337 filed Dec. 6, 2005 and JP Patent Appln. No. 2006-277934 filed Oct. 11, 2006, the contents of all of which are incorporated herein by reference.

TECHNICAL FIELD

The present invention relates to fermented soybean hypocotyl containing equol and a method of producing the same.

BACKGROUND ART

Isoflavones (soybean isoflavones: daidzein, genistein, glycitein) contained in soybeans have structures similar to estradiol, and have anti-estrogen actions associated with binding to estrogen receptors (hereinafter referred to as ER) and estrogen-like actions. The epidemiological studies and intervention studies of soybean isoflavones that have been done before suggest their preventive effects due to their anti-estrogen actions on breast cancer, prostate cancer and other hormone-dependent cancers and improving effects due to estrogen-like actions on menopausal disorders, postmenopausal osteoporosis and hyperlipidemia.

Recently, it has been pointed out that the active principle of the physiological effects of these soybean isoflavones may be a metabolite of daidzein, equol. More specifically, it has been reported that equol has an ability to bind to ER (especially to ERβ) greater than soybean isoflavones and that it has remarkably high transition capability to target organs such as breast and prostate tissues. Moreover, a case-control study reports that there are significantly less patients who produce equol in the patients of breast cancer and prostate cancer. The effects of soybean isoflavones to improve the bone density and lipid metabolism were examined regarding postmenopausal women categorized into two groups: those who produce equol and those who do not. A significant improvement in those who produce equol was observed.

Equol is produced by metabolism of daidzein by enteric bacteria. The abilities to produce equol vary between individuals, and the percentage of Japanese who produce equol production is reportedly about 50%. That is, about 50% of Japanese are not able to produce equol (non-equol-producing individuals). Such an individual cannot enjoy useful physiological benefits based on the action of equol even if they ingest soybeans and processed soybean foods. Therefore, in order to attain useful physiological benefits based on the action of equol in a non-equol-producing individual, ingesting equol itself is thought to be effective.

A known method of producing equol is subjecting a raw material containing daidzein compounds to fermentation treatment by microorganisms (hereinafter referred to as equol-producing bacteria) which metabolize daidzein to produce equol. Known starting materials containing daidzein for use in this production method include soybeans, Ge Gen Tang (Chinese traditional medicine, also known as Kakkonto), red globe grapes, alfalfa or others. Moreover, equol-producing bacteria are already known. For example, bacteroides E-23-15 (FERM BP-6435), streptococcus E-23-17 (FERM BP-6436), streptococcus A6G225 (FERM BP-6437) and lactococcus 20-92 (FERM BP-10036) have been isolated from human excrement by the inventors of the present invention (refer to patent documents 1 and 2).

However, simply subjecting the above-mentioned starting materials containing daidzein compounds to fermentation treatment by using equol-producing bacteria cannot yield sufficient amount of equol in the fermented product, and there has been the problem that desired useful benefits based on the action of equol cannot be sufficiently expected by ingesting the fermented product as it is.

In contrast, the hypocotyl portions of soybeans have been known to contain isoflavones, saponins and other useful components in a proportion higher than in the cotyledon portions which are used as processed soybean foods, and various uses have been developed for its extract (e.g., patent document 3). However, soybean hypocotyl extract itself is disadvantageously expensive. Moreover, when the soybean hypocotyl extract is used as a starting material for producing equol, addition of other nutrients are necessary to allow fermentation by equol-producing bacteria, which can be another problem. For these reasons, the soybean hypocotyl extract cannot be currently used as a starting material for industrially producing equol.

Meanwhile, since the soybean hypocotyl itself has a characteristic bitterness, there is a trend to avoid using the substance itself as it is, and much of the soybean hypocotyl is currently disposed. Furthermore, likewise soybean cotyledon portions, soybean hypocotyls contain allergens, therefore the soybean hypocotyl could not be taken by or administer to people suffering from soybean allergy. Therefore, to effectively utilize the soybean hypocotyl itself, it is important to impart added values to increase its usefulness.

[Patent document 1] International Publication WO99/007392
[Patent document 2] International Publication WO2005/000042
[Patent document 3] Japanese Unexamined Patent Publication No. 2002-234844

DISCLOSURE OF THE INVENTION

Problems to be Solved by the Invention

An object of the invention is to provide an equol-containing fermented soybean hypocotyl material that is useful for foods, pharmaceutical preparations, cosmetic products, etc. Another object of the invention is to provide a method for producing an equol-containing fermented soybean hypocotyl material.

Means for Solving the Problem

The present inventors conducted intensive research to achieve the above objects and found that an equol-containing fermented soybean hypocotyl material can be obtained very efficiently by fermenting soybean hypocotyls using at least one microorganism having an equol-producing ability by utilizing at least one daidzein compound. The present inventors also found that the thus-obtained equol-containing fermented soybean hypocotyl material is useful as an allergen-reduced material, because the allergens contained in the soy bean hypocotyl are reduced. The present invention has been accomplished based on these finding.

In other words, the present invention provides equol-containing fermented soybean hypocotyl materials and uses thereof as below:

Item 1: An equol-containing fermented soybean hypocotyl material obtained by fermenting soybean hypocotyls using at least one microorganism having an equol-producing ability by utilizing at least one daidzein compound selected from the group consisting of diadzein glycosides, daidzein, and dihydrodaidzein.

Item 2: A fermented soybean hypocotyl material according to Item 1, wherein said at least one microorganism is a lactic acid bacterium of the genus *Lactococcus*.

Item 3: A fermented soybean hypocotyl material according to Item 1, wherein said at least one microorganism belongs to *Lactococcus garvieae*.

Item 4: A fermented soybean hypocotyl material according to Item 1, which contains 0.1 to 20 wt % of equol per total weight of dry fermented soybean hypocotyl material.

Item 5: A fermented soybean hypocotyl material according to Item 1, which further contains daidzin compounds, genistin compounds, genistei compounds, glyciti compounds and glycitei compounds.

Item 6: A fermented soybean hypocotyl material according to Item 1, which further contains ornithine.

Item 7: A food containing a fermented soybean hypocotyl material of Item 1.

Item 8: A food according to Item 7, which is a dietary supplement.

Item 9: A food according to Item 7, which contains 0.1 to 90 g of the fermented soybean hypocotyl material per 100 g of the food.

Item 10: A pharmaceutical preparation containing a fermented soybean hypocotyl material of Item 1.

Item 11: A pharmaceutical preparation according to Item 10, which is used for preventing or treating menopausal disorders, osteoporosis, prostatic hypertrophy, or metabolic syndrome.

Item 12: A pharmaceutical preparation according to Item 10, which is used for lowering the blood cholesterol level.

Item 13: Use of a fermented soybean hypocotyl material of Item 1 for producing preparations for preventing or treating menopausal disorders, osteoporosis, prostatic hypertrophy, or metabolic syndrome.

Item 14: Use of a fermented soybean hypocotyl material of Item 1 for producing preparations for lowering the blood cholesterol level.

Item 15: A method for treating menopausal disorders comprising the step of administering an effective amount of a fermented soybean hypocotyl material of Item 1 to a patient suffering from menopausal disorders.

Item 16: A method for lowering the blood cholesterol level comprising the step of administering an effective amount of a fermented soybean hypocotyl material of Item 1 to a patient who is in need of lowering the blood cholesterol level.

Item 17: A cosmetic product containing the fermented soybean hypocotyl material of Item 1.

Item 18: A cosmetic product according to Item 17, which contains 0.1 to 10 g of the fermented soybean hypocotyl material per 100 g of the cosmetic product.

The present invention also provides a method for producing an equol-containing fermented soybean hypocotyl material as below:

Item 19: A method for producing an equol-containing fermented soybean hypocotyl material comprising the step of fermenting soybean hypocotyls using at least one microorganism having an equol-producing ability by utilizing at least one daidzein compound selected from the group consisting of diadzein glycosides, daidzein, and dihydrodaidzein.

Effects of the Invention

The fermented soybean hypocotyl material of the invention contains equol and other active ingredients, such as isoflavones and saponins, and can thereby find a variety of applications in the food, pharmaceutical, cosmetic and other fields. The fermented soybean hypocotyl material of the invention, in particular, has a significantly higher equol content than those of the materials obtained by fermenting a raw material containing daidzein compounds such as soybean, Ge Gen Tang (Chinese traditional medicine, also known as Kakkonto), red globe grapes, alfalfa, and the like, and can thereby attain much superior equol-derived active physiological effects.

Furthermore, because the thus-obtained fermented soybean hypocotyl material is reduced in the amount of the allergens inherently contained in soy bean hypocotyls, it can be safely taken by or administered to people suffering from soybean allergy. Moreover, the fermented soybean hypocotyl material of the invention is made from soybean hypocotyls that are discarded during soybean food processing, and therefore has high industrial potential in terms of effective use of resources.

BEST MODE FOR CARRYING OUT THE INVENTION

Figure 1:
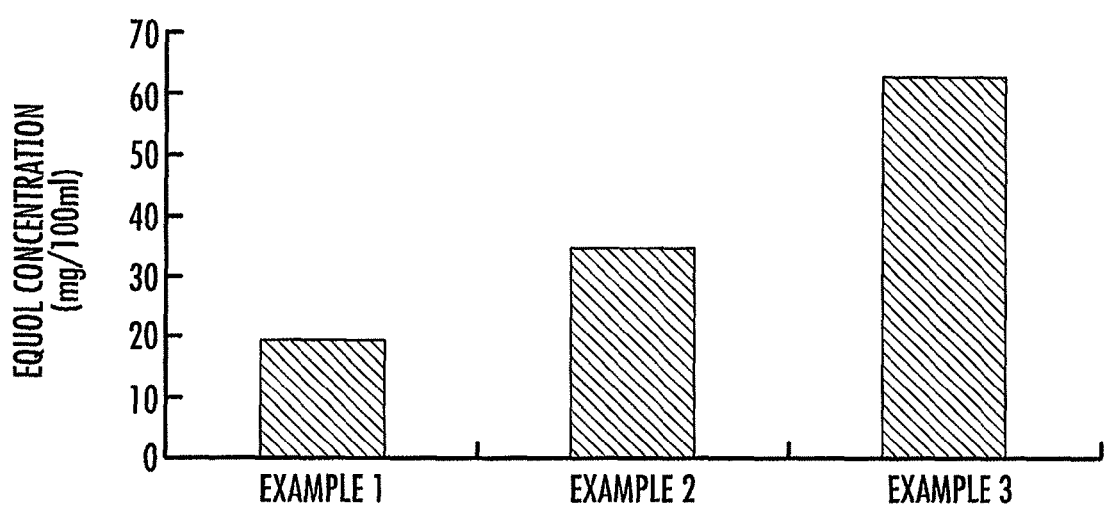
FIG. 1 shows the equol concentrations of the fermented liquids obtained in Examples 1 to 3.

Embodiments of the present invention are described below in detail.

Microorganisms having an ability to produce equol (metabolic activity) by utilizing at least one daidzein compound selected from the group consisting of diadzein glycosides, daidzein, and dihydrodaidzein are used as equol-producing bacteria in the present invention. Specific examples of diadzein glycosides include daidzin, malonyldaidzin, acetyldaidzin, etc.

Such microorganisms (equol-producing bacteria) are not particularly limited as long as they have equol-producing ability and are acceptable for foods, pharmaceuticals, or cosmetics. It has been revealed that microorganisms having the above-mentioned include, for example, bacteria of the genus *Lactococcus*, such as *Lactococcus garvieae*, etc.; bacteria of the genus *Streptococcus*, such as *Streptococcus intermedius*, *Streptococcus constellatus*, etc.; and bacteria of the genus *Bacteroides* such as *Bacteroides ovatus*. Amongst equol-producing bacteria, lactic acid bacteria belonging to the genera *Lactococcus*, *Streptococcus*, etc. are preferable; lactic acid bacteria of the genus *Lactococcus* are particularly preferable; and *Lactococcus garvieae* is particularly preferable. Bacteria having equol-producing ability can be isolated from human feces using the presence or absence of equol production as an indicator. Equol-producing bacteria isolated from human feces and identified by the present inventors, as well as others, i.e., *Lactococcus* 20-92 (FERM BP-10036), *Streptococcus* E-23-17 (FERN BP-6436), *Streptococcus* A6G225 (FERN BP-6437), and *Bacteroides* E-23-15 (FERN BP-6435) have been deposited. Such deposited bacteria can be used in the present invention. Among these, *Lactococcus* 20-92 is preferable.

In the present invention, soybean hypocotyls are used as a fermentation material. Soybean hypocotyls are portions that develop into plumules and radicles when the soybeans germinate, and are known to contain large amounts of daidzein compounds such as daidzein glycosides, daidzein, etc. Soybean hypocotyls for use in the present invention are not limited in origin, and may be processed or unprocessed, as long as their daidzein compound contents are not lost. Usable examples include raw soybean hypocotyls; hypocotyls separated from heated, dried, steamed or otherwise treated soybeans; materials obtained by heating, drying, steaming or otherwise treating hypocotyls separated from unprocessed soybeans. Soybean hypocotyls that have been subjected to removal of fat and/or protein are also usable in the present invention. The form of the soybean hypocotyls for use in the present invention is also not limited, and may be powdered, ground or crushed. From the viewpoint of efficient production of equol, it is preferable to use powdered soybean hypocotyls.

Such soybean hypocotyls are fermented by adding a suitable amount of water to the soybean hypocotyls to adjust the water content, and inoculating equol-producing bacteria as mentioned above.

The amount of water added to the soybean hypocotyls can be suitably selected according to the type of equol-producing bacteria, the type of fermentation tank, etc. It is usually appropriate that, at the start of fermentation, water be present with soybean hypocotyls in a proportion of 400 to 4000 parts by weight, preferably 500 to 2000 parts by weight, and more preferably 600 to 1000 parts by weight, per 100 parts by weight of soybean hypocotyls (on a dry weight basis).

In order to improve the fermentation efficiency, flavor and taste of the fermented product, etc., nutritional ingredients can be added, as necessary, to the soybean hypocotyls used as a fermentation material. Examples of usable nutritional ingredients include yeast extracts, polypeptones, meat extracts, and other nitrogen sources; glucose, sucrose, and other carbon sources; phosphate, carbonate, sulfate, and other mineral salts; vitamins; amino acids; etc. In particular, when using a microorganism having an ability to convert arginine to ornithine (hereinafter referred to as "ornithine/equol-producing microorganism") as an equol-producing microorganism, it is possible to obtain a fermented material containing ornithine by adding arginine to soybean hypocotyls and then performing fermentation. In such a case, the amount of added arginine may be, for example, about 0.5 to about 3 parts by weight per 100 parts by weight of soybean hypocotyls (on a dry weight basis). Equol-producing microorganisms having an ability to convert arginine to ornithine can be selected from *Lactococcus garvieae* strains, and specific examples include *Lactococcus* 20-92 (FERM BP-10036).

The pH of the fermentation material (starting material which is subjected to fermentation) is not limited as long as the equol-producing bacteria are viable. From the viewpoint of good proliferation of equol-producing microorganisms, it is desirable to adjust the pH of the fermentation material to about 6 to about 7, and preferably about 6.3 to about 6.8.

Isoflavones (including daidzein compounds as mentioned above) can be added to the fermentation material. Addition of isoflavone(s) to the fermentation material makes it possible to increase the equol content of the resulting fermented soybean hypocotyl material, improving the utility of the fermented soybean hypocotyl material.

The fermentation of soybean hypocotyls is performed under environmental conditions that are suitable for the growth characteristics of the equol-producing bacteria used. For example, when using the equol-producing bacteria specifically listed above, the fermentation (cultivation) is performed under anaerobic conditions.

The fermentation temperature is not limited as long as it is suitable for the growth of the equol-producing bacteria, and may be, for example, 20 to 40° C., preferably 35 to 40° C., and more preferably 36 to 38° C.

The fermentation time can be suitably selected according to the amount of equol produced, the residual amount of daidzein compounds, the type of equol-producing microorganism, etc., and it is usually 1 to 10 days, preferably 2 to 7 days, and more preferably 3 to 5 days.

Equol is produced and accumulated in the fermented soybean hypocotyl material produced by a fermentation treatment under the conditions mentioned above, and thus the fermented soybean hypocotyl material is capable of exhibiting the useful physiological activity of equol. The equol content of such a fermented soybean hypocotyl material varies depending on the equol-producing bacteria used, fermentation conditions, etc.; and equol is usually contained in an amount of 0.1 to 1 g, preferably 0.2 to 1 g, and more preferably 0.5 to 0.8 g, per 100 g, on a dry weight basis, of fermented soybean hypocotyl material.

The fermented soybean hypocotyl material contains various isoflavones other than equol, such as daidzin, malonyldaidzin, acetylmalonyldaidzin, daidzein, dihydrodaidzein, and other daidzein compounds (these components may be referred to as "daidzein compounds"); genistin, malonylgenistin, acetylgenistin, genistein, dihydrogenistein, and other genistein compounds (these components may be referred to as "genistein compounds"); glycitin, malonylglycitin, acetylglycitin, glycitein, dihydroglycitein, and other glycitein compounds (these components may be referred to as "glycitein compounds"); etc. Thus, the fermented material also exhibits the useful physiological activities of such isoflavones. The isoflavone (including equol) content of the fermented soybean hypocotyl material may be, for example, on a dry weight basis, about 0.5 to about 2 g, preferably about 0.5 to about 1.5 g, and more preferably about 0.8 to about 1.5 g, per 100 g of the fermented soybean hypocotyl material.

The proportions of isoflavones other than equol in the fermented soybean hypocotyl material are different from those in unfermented soybean hypocotyls. In particular, in the fermented soybean hypocotyl material, the total content of genistein compounds, whose activities as endocrine disrupters raise concerns, is as low as 14 wt. % or less, and preferably 12 wt. % or less. Therefore, the fermented soybean hypocotyl material is also more advantageous than unfermented soybean hypocotyls from the viewpoint of isoflavone proportions.

Specific examples of proportions of isoflavones in the fermented soybean hypocotyl material include the following, in which "mg" indicates the total content of each isoflavone per 1 g of fermented soybean hypocotyl material on a dry weight basis.
Equol: 1 to 20 mg, and preferably 2 to 10 mg;
Daidzein compounds: 0.1 to 3 mg, and preferably 0.1 to 1.5 mg;
Genistein compounds: 0.05 to 2.5 mg, and preferably 0.05 to 2 mg;
Glycitein compounds: 0.1 to 4 mg, and preferably 2 to 3.5 mg.

The proportions of these isoflavones contained in the fermented soybean hypocotyl material are, for example, as below, in which "wt. %" indicates the percentage relative to the total amount of isoflavones contained in the fermented soybean hypocotyl material.
Equol: 30 to 75 wt. %, preferably 40 to 70 wt. %, and more preferably 45 to 65 wt. %;

Daidzein compounds: 1 to 20 wt. %, preferably 2 to 15 wt. %, and more preferably 4 to 8 wt. %;
Genistein compounds: 0.1 to 20 wt. %, preferably 1 to 15 wt. %, and more preferably 1 to 10 wt. %;
Glycitein compounds: 10 to 50 wt. %, preferably 15 to 35 wt. %, and more preferably 25 to 30 wt. %;

The fermented soybean hypocotyl material of the present invention contains isoflavones in such proportions that cannot be achieved by known methods. Therefore, the fermented soybean hypocotyl material of the present invention may be referred to as an isoflavone-containing material comprising the isoflavones in the above proportions.

For production of a fermented soybean hypocotyl material having an isoflavone proportions as above, *Lactococcus* 20-92 (FERN BP-10036) can be used particularly advantageously.

Further, since the fermented soybean hypocotyl material also contains saponins derived from soybean hypocotyls, it is also possible to achieve the useful physiological activity based on such saponins (e.g., antiviral activity). The saponin content of the fermented soybean hypocotyl material is usually 1 to 8 g, preferably 2 to 5 g, and more preferably 3 to 4 g, per 100 g, on a dry weight basis, of the fermented soybean hypocotyl material.

Further, as mentioned above, ornithine is contained in a fermented soybean hypocotyl material obtained by adding arginine to soybean hypocotyls and performing fermentation using an ornithine/equol-producing microorganism. Specifically, ornithine may be contained in such a fermented soybean hypocotyl material in an amount of, for example, about 0.5 to about 2.0 g, preferably about 0.8 to about 1.5 g, and more preferably about 0.9 to about 1.2 g, per 100 g, on a dry weight basis, of the fermented soybean hypocotyl material.

The fermented soybean hypocotyl material obtained by fermentation under the conditions described above may be in its post-fermentation state without additional treatment, or may be dried as necessary to form a dry solid product, for use as an ingredient for foods, pharmaceuticals, cosmetics, etc. In order to improve its storage stability, the fermented soybean hypocotyl material is preferably dried to solid form. The heated and dried fermented soybean hypocotyl material may be powdered, as necessary.

As previously described, because the fermented soybean hypocotyl material of the invention contains a variety of effective physiologically active substances such as equol, it expresses a variety of physiological and pharmacological activities. For example, the fermented soybean hypocotyl material of the invention is useful for the prevention or alleviation of symptoms or diseases such as, e.g., menopausal disorders, osteoporosis, prostatic hypertrophy, metabolic syndrome, and for lowering of the blood cholesterol level, skin whitening, acne treatment, treatment of intestinal disorders, obesity, urinary disorders, etc. Among such uses, the fermented soybean hypocotyl material of the invention is especially useful for the prevention or alleviation of general malaise-complaints and menopausal symptoms (for example, osteoporosis, menopausal disorders, etc.) in middle-aged women. When a fermented soybean hypocotyl material is produced by fermenting an arginine-containing fermentation material using an ornithine/equol-producing bacteria, ornithine is also formed and stored therein. Such a fermented soybean hypocotyl material can also exhibit active physiological effects derived from ornithine, such as improved liver function, improved growth hormone secretion, increased immunostimulation, increased amount of muscles, increased basal metabolism, etc.

When the fermented soybean hypocotyl material of the invention is used as a food ingredient, it may be prepared in the form of, e.g., a drink, granules, fine grains, capsules, tablets, a powder, dairy product, gum, gum drop, pudding, bar, or other solid food. A food containing the fermented soybean hypocotyl material exhibits not only the equol-derived effective physiological activities, but also physiological activies derived from isoflavones, saponins, and other like materials. Such foods, therefore, provide excellent health-keeping effects, and are highly useful. When a fermented soybean hypocotyl material produced by fermenting an arginine-containing fermentation material using ornithine/equol-producing bacteria is used in a food, such a food also contains ornithine, and therefore has further enhanced usefulness.

Food containing the fermented soybean hypocotyl material of the invention are usable, not only as general foods, but also as foods for specified health uses, dietary supplements, functional foods, foods for invalids, etc. Foods containing the fermented soybean hypocotyl material of the invention are particularly usable as dietary supplements.

The proportion of the fermented soybean hypocotyl material of the invention in a food can be suitably determined according to the type of food, equol content, age and sex of the subject, expected effects, and other factors. For example, the total amount of the fermented soybean hypocotyl material per 100 g of a food may be generally 0.1 to 90 g, preferably 0.1 to 10 g, and more preferably 0.5 to 2 g on a dry weight basis.

The daily dosage of a food containing the fermented soybean hypocotyl material depends upon the equol content of the fermented soybean hypocotyl material, age and body weight of the subject, daily number of doses, and other factors; but, for example, an adult may take a daily dosage of 0.1 to 10 g of the fermented soybean hypocotyl material.

When the fermented soybean hypocotyl material of the invention is used as a pharmaceutical ingredient, the fermented soybean hypocotyl material is prepared in the form of, e.g., tablets, pills, a powder, a liquid medicine, a suspension, an emulsion, granules, capsules, a suppository, or the like. A pharmaceutical preparation containing the fermented soybean hypocotyl material of the invention is useful for the prevention or alleviation of symptoms or diseases, e.g., menopausal disorders (including menopausal complaints, osteoporosis, and hyperlipidemia), osteoporosis, prostatic hypertrophy, metabolic syndrome, and for the reduction of the blood cholesterol level, treatment of intestinal disorders, obesity, urinary disorders, etc. Such a pharmaceutical preparation is especially suitable for use in the prevention or treatment of general malaise-complaints and menopausal symptoms (e.g., osteoporosis, menopausal disorders, etc.) in middle-aged women.

The dosage of a pharmaceutical preparation containing the fermented soybean hypocotyl material of the invention depends upon the equol content of the fermented soybean hypocotyl material, age and body weight of the subject, symptoms, number of doses per day, and other factors; but, for example, an adult may take a daily dosage of 0.5 to 6 g of the fermented soybean hypocotyl material on a dry weight basis.

When the fermented soybean hypocotyl material of the invention is used as a cosmetic ingredient, the fermented soybean hypocotyl material may be prepared in any desired form, such as, e.g., paste-like, mousse-like, gel-like, liquid, emulsion, suspension, cream, ointment, sheet-like, or like form. Such cosmetic products can be used in a wide various usages: e.g., basic skin care products such as emulsions, creams, lotions, oils, and packs; cleansing products such as facial washes, cleansers, and body cleansers; cleansing wipes; purifying agents; etc. Cosmetic products containing the fermented soybean hypocotyl material of the invention are used for skin whitening and clearing acne.

The proportion of the fermented soybean hypocotyl material of the invention in a cosmetic product can be suitably determined according to the type of the cosmetic product, equol content, and the like. For example, the total amount of the fermented soybean hypocotyl material per 100 g of a food may be 0.1 to 10 g, and preferably 0.5 to 5 g on a dry weight basis.

EXAMPLES

The present invention is described in detail with reference to Test Examples, Examples, etc. below, but is not limited to these examples.

Examples 1 to 3

Powdered soybean hypocotyls, arginine, and water were mixed in such a manner that the compositions of the mixture was as shown in Table 1 to prepare soybean hypocotyl solutions. Into 5 ml samples of the soybean hypocotyl solution was inoculated *Lactococcus* 20-92 (FERN BP-10036; *Lactococcus garvieae*), and subjected to static cultivation at 37° C. for 96 hours under anaerobic conditions. After cultivation, the resulting culture (fermented liquids) were sterilized by heating at 100° C. for one minute, subsequently dried at 80° C., and further powdered using a homogenizer, thereby obtaining powdered fermented soybean hypocotyl materials.

Table 1 shows equol concentrations in culture 96 hours after cultivation. Table 1 also shows viable bacterial counts and pH of culture media 96 hours after cultivation, yields of the powdered fermented soybean hypocotyl materials, and equol concentrations in the powdered fermented soybean hypocotyl materials. The results established that fermentation of the powdered soybean hypocotyls using an equol-producing bacterium can produce equol very efficiently.

rial (referred to as "post-fermentation" in Tables 2 and 3) were analyzed for compositional components. Table 2 shows the analytical results for soybean isoflavones, and Table 3 shows the analytical results for nutritional components. These results also established that fermented soybean hypocotyl materials containing high levels of equol can be produced by fermenting soybean hypocotyls with equol-producing bacterium. The results further revealed that the contents of oligosaccharides such as raffinose, stachyose and the like after the fermentation remain almost the same as before, indicating that they are hardly influenced by fermentation. However, it was found that arginine is converted to ornithine by fermentation. Consequently, it was established that when arginine-added soybean hypocotyls are fermented with *Lactococcus* 20-92, not only equol but also ornithine can be produced.

TABLE 2

| | Soybean isoflavones | |
|---|---|---|
| Component | Pre-fermentation | Per 100 g Post-fermentation |
| Equol | N.D. | 632.0 mg |
| Daidzin | 566.4 mg | 29.7 mg |
| Malonyldaidzin | 124.9 mg | N.D. |
| Acetyldaidzin | 364.8 mg | 25.4 mg |
| Daidzein | 7.1 mg | 24.4 mg |
| Dihydrodaidzein | N.D. | 49.4 mg |
| Genistin | 111.7 mg | 3.2 mg |
| Malonylgenistin | 35.1 mg | N.D. |
| Acetylgenistin | 146.1 mg | 3.7 mg |

TABLE 1

| | | Ex. 1 | Ex. 2 | Ex. 3 |
|---|---|---|---|---|
| Composition of soybean hypocotyl solution | Powdered soybean hypocotyls (dried wt.) | 0.25 g | 0.5 g | 0.75 g |
| | Arginine | 0.005 g | 0.005 g | 0.005 g |
| | Water | Appropriate quantity | Appropriate quantity | Appropriate quantity |
| | Total amount | 5 ml | 5 ml | 5 ml |
| | pH | 6.75 ± 0.03 | 6.54 ± 0.02 | 6.39 ± 0.03 |
| Analytical result of fermented liquid | Viable bacterial counts of fermented liquid (log cfu/ml) | 7.9 ± 0.1 | 8.2 ± 0.1 | 8.3 ± 0.2 |
| | pH of fermented liquid | 7.00 ± 0.03 | 6.88 ± 0.01 | 6.76 ± 0.02 |
| Analytical result of powered fermented soybean hypocotyls | Equol concentration in powdered soybean hypocotyl material (mg/100 g) | 385.6 ± 101.5 | 344.6 ± 62.1 | 417.5 ± 68.0 |

Note:
Each example was carried out using powdered soybean hypocotyls of three different lots (N = 3). The analytical results in the table are average ± SD values.

Example 4

*Lactococcus* 20-92 (FERN BP-10036; *Lactococcus garvieae*) was inoculated into 5 ml of a soybean hypocotyl solution containing 10 wt. % of powered soybean hypocotyls and 0.1 wt. % of L-arginine, and subjected to static cultivation at 37° C. for 96 hours under anaerobic conditions. After cultivation, the resulting culture (fermented liquid) was sterilized by heating at 100° C. for one minute, then dried at 80° C., and further powdered using a homogenizer, thereby obtaining a powered fermented soybean hypocotyl material.

The powdered soybean hypocotyls used as starting materials (referred to as "pre-fermentation" in Tables 2 and 3) and the obtained powdered fermented soybean hypocotyl mate-

TABLE 2-continued

| | Soybean isoflavones | |
|---|---|---|
| Component | Pre-fermentation | Per 100 g Post-fermentation |
| Genistein | 0.9 mg | 22.5 mg |
| Dihydrogenistein | N.D. | 112.0 mg |
| Glycitin | 331.7 mg | 53.6 mg |
| Malonylglycitin | 65.0 mg | N.D. |
| Acetylglycitin | 169.2 mg | 34.8 mg |
| Glycitein | 19.1 mg | 292.3 mg |

TABLE 2-continued

Soybean isoflavones

| Component | Pre-fermentation | Per 100 g Post-fermentation |
|---|---|---|
| Dihydroglycitein | N.D. | 8.2 mg |
| Total isoflavones | 1942.0 mg | 1291.2 mg |

N.D. refers to "Not Detected"

TABLE 3

Nutritional component

| Component | Pre-fermentation | Per 100 g Post-fermentation |
|---|---|---|
| Moisture | 3.2 g | 6.2 g |
| Protein | 38.1 g | 38.3 g |
| Fat | 13.0 g | 14.5 g |
| Ash | 4.3 g | 4.0 g |
| Saccharide | 30.9 g | 26.8 g |
| Dietary fiber | 10. g | 10.2 g |
| Energy | 414 kcal | 411 kcal |
| Sucrose | 7.95 g | 7.42 g |
| Raffinose | 1.37 g | 1.34 g |
| Stachyose | 9.04 g | 8.38 g |
| Trans fatty acids | N.D. | N.D. |
| Phospholipids(as stear-, ole-, and lecitin) | 3.33 g | 2.92 g |
| Free arginine | 881 mg | 12 mg |
| Free ornithine | N.D. | 1.06 g |
| Syasapogenol A | N.D. | N.D. |
| Soyasapogenol B | N.D. | N.D. |
| Soybean saponine | 3.6 g | 3.8 g |

N.D. refers to "Not Detected"

Examples 5-11

Powdered fermented soybean hypocotyls (Examples 5-11) were produced under the same conditions as in Example 3, except that powdered soybean hypocotyls of seven different lots from that in Example 3 were used. Proportions of isoflavones contained in the thus-obtained fermented soybean hypocotyl materials were evaluated. As is clear from the results shown in Table 4, the fermented soybean hypocotyl materials of Examples 5-11 have a high equol content and contain isoflavones in such proportions that cannot be achieved by known methods.

In Table 4, the upper figures indicate the amount (mg) of each isoflavone per 1 g of fermented soybean hypocotyl material, and the lower figures indicate the percentage (wt %) of each isoflavone per total weight (100% wt) of isoflavones contained in each fermented soybean hypocotyl material.

Example 12

Powdered fermented soybean hypocotyls were produced under the same conditions as in Example 3 above, except that powdered soybean hypocotyls of a different lot from that in Example 3 above were used. The obtained fermented soybean hypocotyl material contained 6.5 mg of equol, 0.6 mg of daidzein compounds, 0.6 mg of genistein compounds, and 3.2 mg of glycitein compounds, per g. Aglycone accounted for 90 wt. % or more in the total isoflavone content in the fermented soybean hypocotyl material.

Tablets having the following formula (weight 2.51 g and 10.9 mg equol content per tablet) were prepared using the thus obtained fermented soybean hypocotyls.

| Fermented soybean hypocotyl material | 66.7 wt. % |
|---|---|
| Erythritol | 33.2 wt. % |
| Total | 100.0 wt. % |

Example 13

Granules having the following formula were prepared using the fermented soybean hypocotyl material used in Example 5 above.

| Fermented soybean hypocotyl material | 66.7 wt. % |
|---|---|
| Erythritol | 33.2 wt. % |
| Total | 100.0 wt. % |

Example 14

Cosmetic product having the following formula were prepared using the fermented soybean hypocotyl material of Example 1 above.

TABLE 4

Isoflavone Proportions

| | Equol | Daidzein Compounds | Genistein Compounds | Glycitein Compounds |
|---|---|---|---|---|
| Example 5 | 6.51 mg (62.2 wt. %) | 0.71 mg (6.8 wt. %) | 0.53 mg (5.1 wt. %) | 2.71 mg (25.9 wt. %) |
| Example 6 | 6.25 mg (61.3 wt. %) | 0.48 mg (4.7 wt. %) | 0.35 mg (3.4 wt. %) | 3.12 mg (30.6 wt. %) |
| Example 7 | 5.38 mg (48.9 wt. %) | 1.18 mg (10.7 wt. %) | 1.45 mg (13.2 wt. %) | 3.00 mg (27.2 wt. %) |
| Example 8 | 6.43 mg (63.4 wt. %) | 0.61 mg (6.0 wt. %) | 0.48 mg (4.7 wt. %) | 2.62 mg (25.8 wt. %) |
| Example 9 | 6.05 mg (64.2 wt. %) | 0.51 mg (5.4 wt. %) | 0.30 mg (3.2 wt. %) | 2.57 mg (27.3 wt. %) |
| Example 10 | 6.11 mg (65.6 wt. %) | 0.37 mg (4.0 wt. %) | 0.10 mg (1.1 wt. %) | 2.74 mg (29.4 wt. %) |
| Example 11 | 6.3 mg (60.9 wt. %) | 0.49 mg (4.73 wt. %) | 0.37 mg (3.6 wt. %) | 3.19 mg (30.8 wt. %) |

| | |
|---|---|
| Fermented soybean hypocotyl material | 10 g |
| Paraffin oil | 60 ml |
| Olive oil | 40 ml |
| Glycerol monostearic acid ester | 50 ml |
| Lanolin | 10 ml |
| propylene glycol | 30 ml |
| Water | balance |
| Total | 1000 g |

Example 15

Cosmetic product having the following formula were prepared using the fermented soybean hypocotyl material of Example 1 above.

| | |
|---|---|
| Fermented soybean hypocotyl material | 10 g |
| Paraffin oil | 30 ml |
| Olive oil | 30 ml |
| Glycerol monostearic acid ester | 60 ml |
| Lanolin | 20 ml |
| propylene glycol | 40 ml |
| Water | balance |
| Total | 1000 g |

Test Example 1

It is known that soybean hypocotyls inherently contain Gym4, Gm30K, Gm28K, 7S globulin mix (β-conglycine), oleocine, trypsin inhibitor and like allergens. The presence or absence of allergens in the fermented soybean hypocotyl material prepared in Example 1 was detected by the following method.

First, an adequate amount of the fermented soybean hypocotyl material prepared in Example 1 was added to an extraction buffer (Tris HCl pH 7.5, containing 1 M EDTA and an adequate amount of protease inhibitor), followed by sufficient agitation to extract water-soluble components from the fermented soybean hypocotyl material. Subsequently, solid matter was removed therefrom by filtration, giving an extract. Total protein in the thus-obtained extract was assayed using a Bio-Rad Protein Assay. Major allergens (Gym4, Gm30K, Gm28K, 7S globulin mix, oleocine, and trypsin inhibitor) contained in the thus-obtained extract were then detected by western blotting. For comparison, detections of total protein and major allergens were conducted in the same manner as described above using soybean cotyledon and soybean hypocotyl powders instead of the fermented soybean hypocotyl material.

Figure 2:
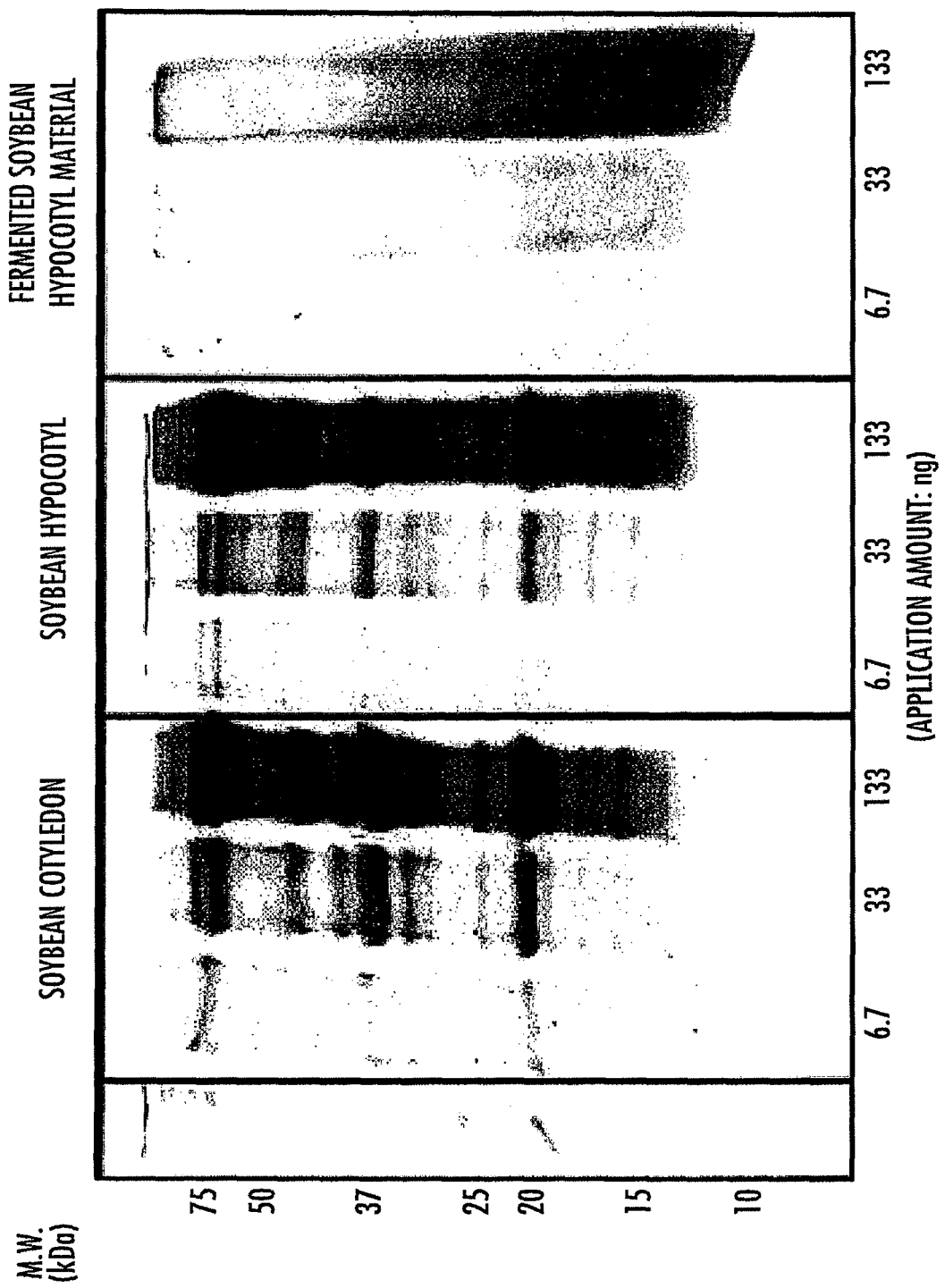
FIG. 2 shows the detection results of total proteins contained in the fermented soybean hypocotyl material of Example 1, soybean cotyledons, and soybean hypocotyls (electrophoretogram).
Figure 3:
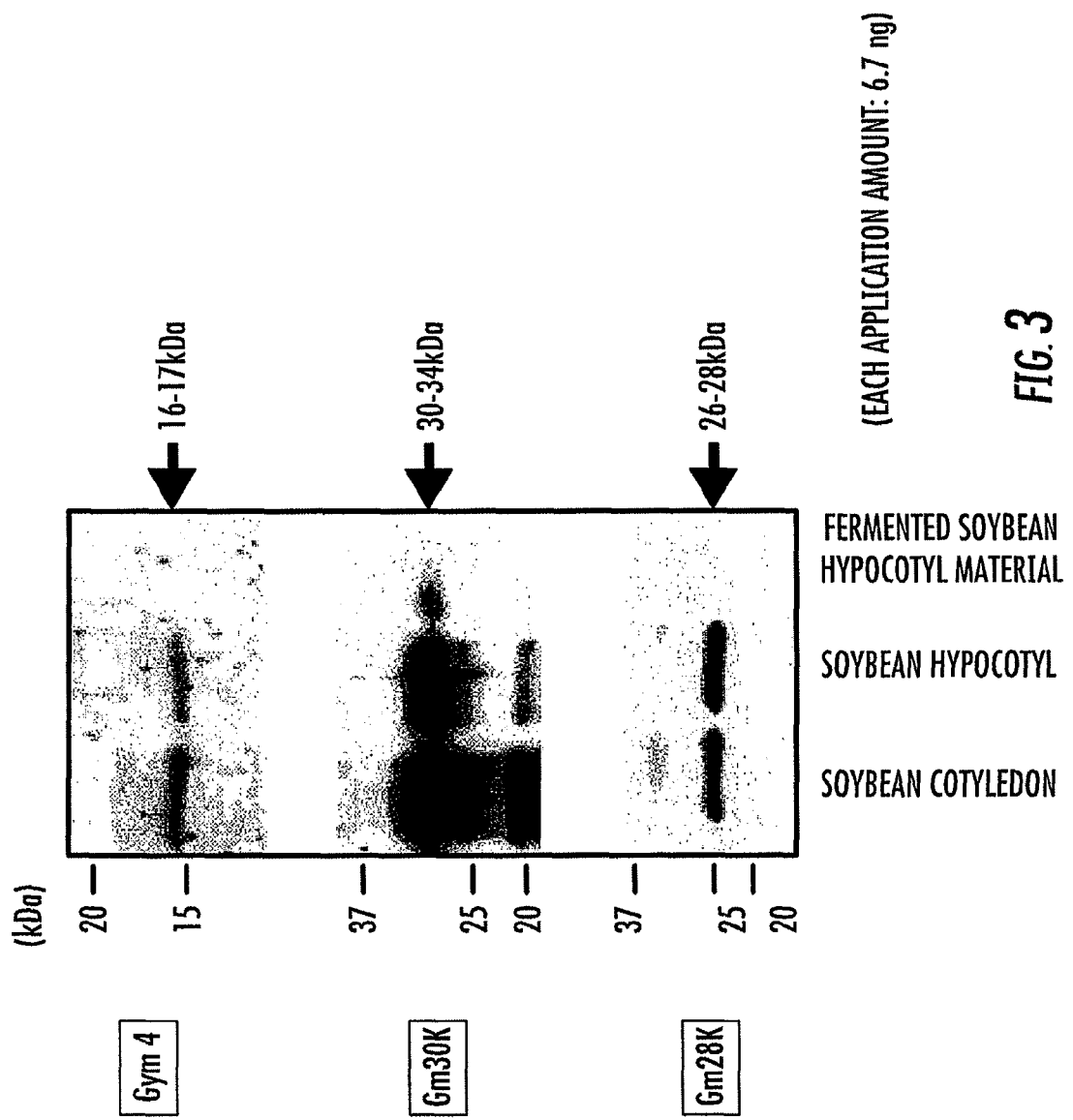
FIG. 3 shows the detection results of major allergens (Gym4, Gm30K, and Gm28K) contained in the fermented soybean hypocotyl material of Example 1, soybean cotyledons, and soybean hypocotyls (electrophoretogram).
Figure 4:
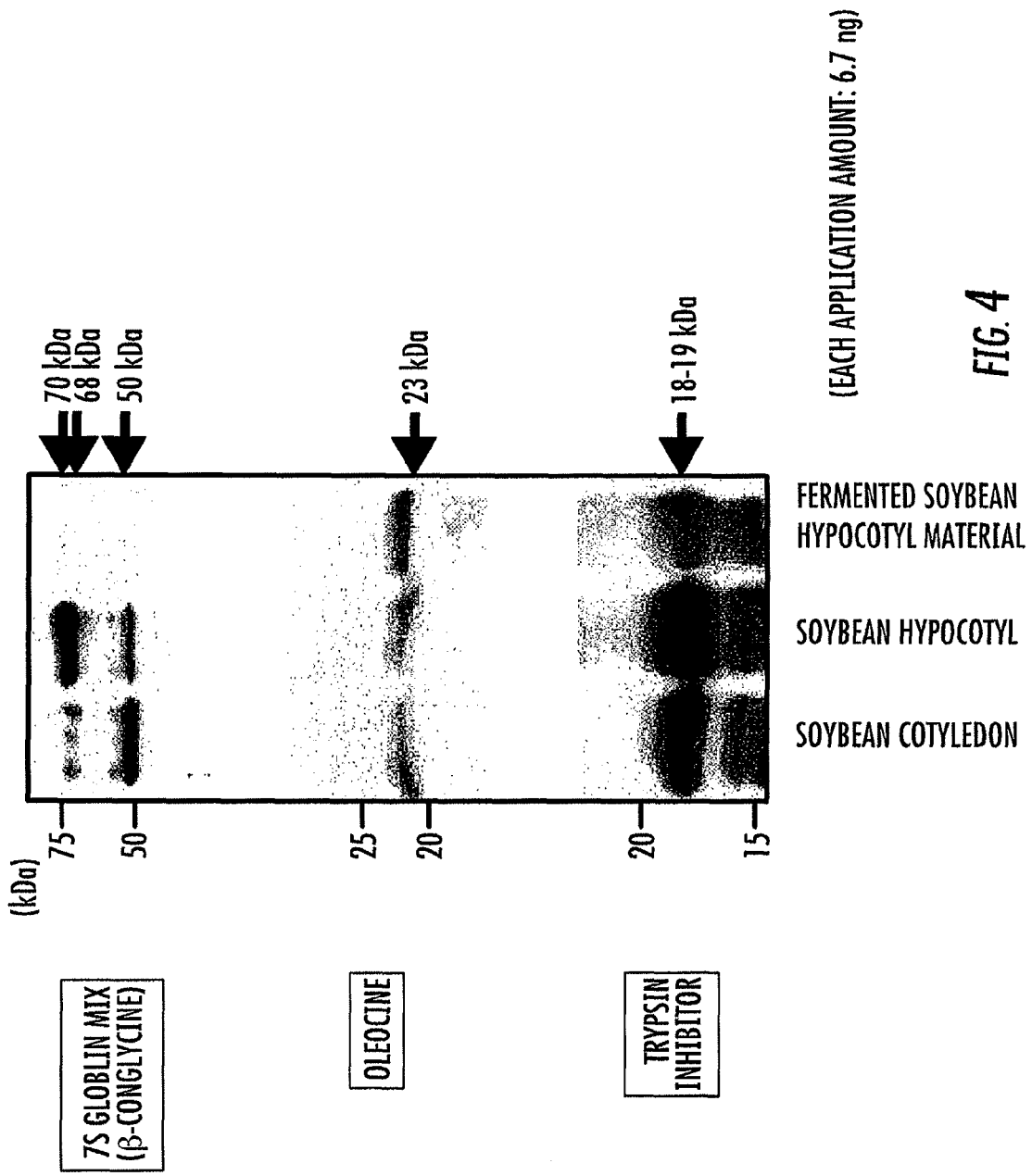
FIG. 4 shows the detection results of major allergens (7S globulin mix, oleocine, and trypsin inhibitor) contained in the fermented soybean hypocotyl material of Example 1, soybean cotyledons, and soybean hypocotyls (electrophoretogram).

FIGS. 2 to 4 show the results. FIG. 2 shows the results of total protein detection. FIG. 3 shows the results of Gym4, Gm30K, and Gm28K detections. FIG. 4 shows the results of 7S globulin mix, oleocine, and trypsin inhibitor detections.

From these results, it was confirmed that major allergens inherently contained in soybeans or soybean hypocotyls are eliminated in the fermented soybean hypocotyl material.

The invention claimed is:

1. Fermented soybean hypocotyl for administration to a human, wherein said fermented soybean hypocotyl comprises the following isoflavones (a) to (d):
   (a) equol, wherein the equol, on a dry weight basis, constitutes 40 to 70 wt % of the total isoflavone content of said fermented soybean hypocotyl;
   (b) at least one daidzein compound selected from the group consisting of daidzin, malonyldaidzin, acetyldaidzin, daidzein and dihydrodaidzein, wherein the at least one daidzein compound, on a dry weight basis, constitutes 1 to 20 wt % of the total isoflavone content of said fermented soybean hypocotyl;
   (c) at least one genistein compound selected from the group consisting of genistin, malonylgenistin, acetylgenistin, genistein and dihydrogenistein, wherein the at least one genistein compound, on a dry weight basis, constitutes 1 to 15 wt % of the total isoflavone content of said fermented soybean hypocotyl; and
   (d) at least one glycitein compound selected from the group consisting of glycitin, malonylglycitin, acetylglycitin, glycitein and dihydroglycitein, wherein the at least one glycitein compound, on a dry weight basis, constitutes 10 to 50 wt % of the total isoflavone content of said fermented soybean hypocotyl,
   wherein the fermented soybean hypocotyl is dried,
   and wherein the fermented hypocotyl comprises 1 to 20 mg of equol per gram of the fermented soybean hypocotyl on a dry weight basis.

2. The fermented soybean hypocotyl according to claim 1, wherein the content of allergen in the soybean hypocotyl is reduced.

3. A food, a dietary supplement, a pharmaceutical product, or a cosmetic product containing the fermented soybean hypocotyl of claim 1.

* * * * *